United States Patent [19]

Niwa et al.

[11] Patent Number: 5,213,112
[45] Date of Patent: May 25, 1993

[54] TENSION METER FOR ORTHOPEDIC SURGERY

[75] Inventors: Shigeo Niwa, Aichi; Mineo Sakakibara, Kanagawa, both of Japan

[73] Assignee: Pfizer Hospital Products Group, Inc., New York, N.Y.

[21] Appl. No.: 827,308

[22] Filed: Jan. 29, 1992

[51] Int. Cl.⁵ ............................................. A61B 5/103
[52] U.S. Cl. ..................................... 128/774; 606/90; 606/99; 73/862.23
[58] Field of Search ....................... 128/774, 782, 781; 606/53, 57, 58, 61, 60, 90, 99, 102, 105, 88; 73/862.23, 862.21, 862.42

[56] References Cited

U.S. PATENT DOCUMENTS

| | | | |
|---|---|---|---|
| 3,805,775 | 4/1974 | Fischer et al. | 606/68 |
| 4,066,082 | 1/1978 | Arcan et al. | 606/92 |
| 4,204,531 | 5/1980 | Aginsky | 606/63 |
| 4,501,266 | 2/1985 | McDaniel | 606/90 |
| 4,545,374 | 10/1985 | Jacobson | 606/90 |
| 4,838,264 | 6/1989 | Bremer et al. | 606/72 |
| 4,898,161 | 2/1990 | Grundei | 606/90 |
| 4,899,761 | 2/1990 | Brown et al. | 128/781 |
| 4,903,691 | 2/1990 | Heinl | 606/70 |
| 4,966,600 | 10/1990 | Songer et al. | 606/74 |
| 5,002,547 | 3/1991 | Poggie et al. | 606/88 |

Primary Examiner—Max Hindenburg
Assistant Examiner—Guy V. Tucker
Attorney, Agent, or Firm—Peter C. Richardson; Lawrence C. Akers; Raymond W. Augustin

[57] ABSTRACT

A tension meter for measuring the degree of tension between bones has a grip portion, a tension meter body mounted to the grip portion, and a torque setting device rotatably connected through a torque shaft to the tension meter body. The tension meter body includes a body portion, a fixed arm extending from one end of the body portion, and a movable arm mounted on the body portion so as to be movable away therefrom. The movable arm is located in opposed relationship to the fixed arm. The movable arm is provided with a gear portion meshing the torque shaft. The torque setting device is provided with a torque limiter for limiting relative displacement of the movable arm in relation to the fixed arm according to a force to be applied between the fixed arm and the movable arm. Use of the tension meter produces quantitative data which makes it possible to carry out surgical operations with reproducible results because they do not rely only upon the surgeon's senses.

8 Claims, 8 Drawing Sheets

PRIOR ART

PRIOR ART

PRIOR ART

TENSION METER FOR ORTHOPEDIC SURGERY

BACKGROUND OF THE INVENTION

1. Field of the Invention

This invention relates to a tension meter for orthopedic surgery for expanding a spacing between bones and measuring a degree of tension between the bones before embedding an artificial joint or implanting an artificial bone between the bones.

2. Description of the Prior Art

In recent years, various new materials such as ceramics have been developed, and skeletal alternative materials having an excellent function have also been proposed in succession. An artificial joint and an artificial bone to be manufactured by using such skeletal alternative materials are widely used in the field of orthopedic surgery at present, and a great remedial effect has been exhibited.

Such an artificial joint or an artificial bone is surgically embedded or implanted into a human body. For example, in the case of substituting the artificial joint for a knee joint, a spacing between bones in the knee joint is set before actually embedding the artificial joint. In this procedure, a distal portion of a femur and a proximal portion of a tibia are first cut away, and then a spacer having a suitable thickness is inserted into the spacing between the femur and the tibia. Under this condition, a surgeon checks the degree of tension of the ligaments connecting the femur and the tibia at opposite side portions of the knee joint by touching the ligaments with his fingers. Further, the surgeon measures the degree of tension of the ligaments with his senses by swinging a leg portion below the tibia in right, left, front and rear directions. As the tensile strength of the ligaments is individually dependent on patients, it is necessary to expand the spacing between the femur and the tibia to a suitable value according to the tensile strength of each patient and stretch the ligaments under a suitable tension, so as to make the artificial joint function properly. Accordingly, various spacers are provided having different thicknesses are used in succession to select an optimum one of these spacers and set the spacing between the femur and the tibia according to the tensile strength of the ligaments of the patient. Thereafter, the selected spacer is removed from the knee joint, and an artificial joint having a size corresponding to the spacing set above is then embedded into the knee joint.

SUMMARY OF THE INVENTION

In the case of substituting the artificial joint for the knee joint or between vertebrae, a degree of tension between the bones is finally measured by the touch of surgeon's fingers to the ligaments. Accordingly, this measurement largely relies on the surgeon's senses, and the selection of the artificial joint having an optimum size is not always accomplished. Further, satisfactory reproduction of the surgical operation cannot be achieved because the lack of past surgical data expeditious selection of the optimum size artificial joint makes it difficult.

Similarly, in the case of implanting the artificial bone between the vertebral bodies, the degree of spreading of the opening between the vertebral bodies relies on X-ray measurements before the surgical operation or the macroscopic measurement of the distance between the vertebral bodies during the surgical operation. Accordingly, sufficient accuracy in determining the degree of spreading cannot be obtained. As a result, whether or not an artificial bone having an optimum size has been selected to be implanted can be determined only according to the progress of the patient after the surgical operation, which is an unsatisfactory method.

This invention has been achieved in view of the above circumstances, and it is an object of the present invention to provide a tension meter which can measure a degree of tension between bones according to quantitative data and makes it possible to carry out a surgical operation with high reproducibility according to this data.

To solve the above problems, there is provided according to the present invention a tension meter for orthopedic surgery for expanding the between two bones and measuring a degree of tension between the bones before embedding an artificial joint or implanting a prosthetic implant therebetween. The tension meter comprises a grip portion, a tension meter body mounted to the grip portion, and a torque setting device rotatably connected through a torque shaft to the tension meter body. The tension meter body comprises a body portion, a fixed arm extending from one end of the body portion on the opposite side of said grip portion. A movable arm is mounted on an upper surface of the body portion so as to be movable away therefrom. The movable arm being located just above said fixed arm in opposed relationship thereto. The movable arm being provided with a gear portion meshing with the torque shaft. The torque setting device includes a torque limiter for limiting relative displacement of the movable arm in relation to the fixed arm according to a force to be applied between the fixed arm and the movable arm.

According to the tension meter for orthopedic surgery of the present invention, a degree of tension of a ligament can be preliminarily set by the torque limiter mechanism on the basis of past data or the like. Accordingly, a spacing between bones can be expanded properly and quantitatively by the fixed arm and the movable arm without reliance upon surgeon's senses as in the prior art.

BRIEF DESCRIPTION OF THE DRAWINGS

In the drawings, wherein similar reference characters denote similar elements throughout the views.

DESCRIPTION OF THE PREFERRED EMBODIMENT

Figure 6:
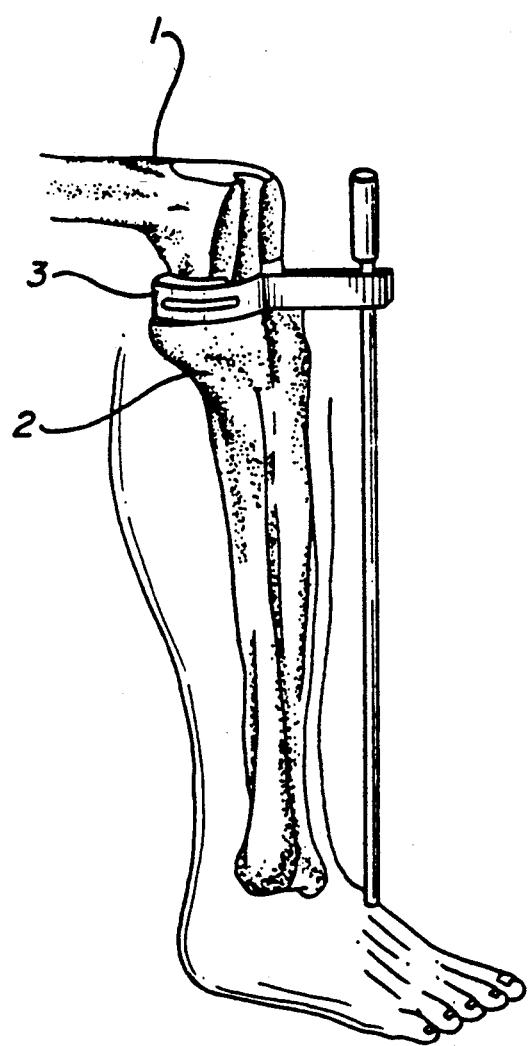
FIG. 6 is a perspective view explaining a conventional method of a surgical operation in the case of substituting an artifical joint for a knee joint.
Figure 7:
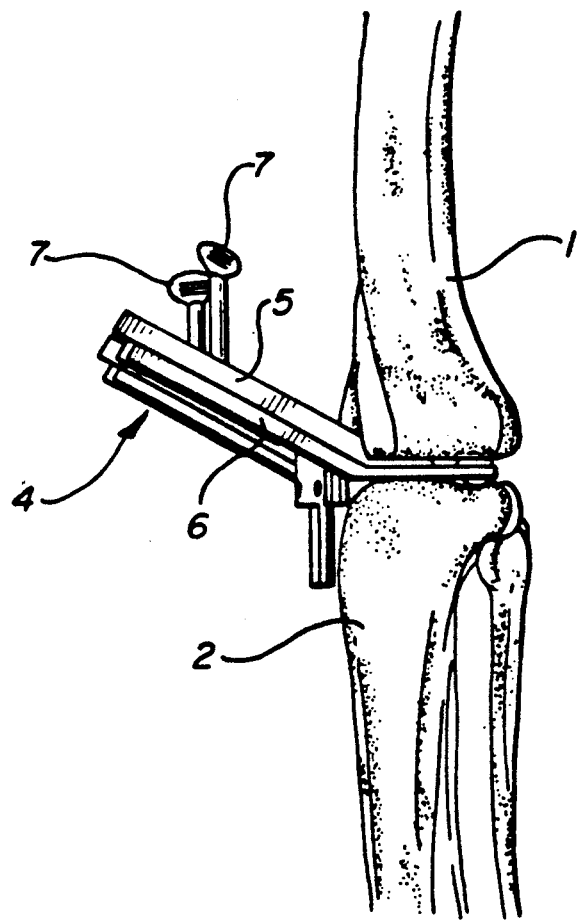
FIG. 7 is a perspective view explaining another conventional method of the surgical operation in the case of substituting an artificial joint for a knee joint.

Referring to FIGS. 6 and 7 there is shown known expanders 4 which have been employed to tension the joint. Spacers 3 of varying thicknesses have been used to set the gap between femur 1 and tibia 2 according to the tension in the ligaments. Thereafter, selected spacer 3 is removed and a prosthetic knee joint having a size corresponding to the opening is implanted. The expander 4 is provided with a pair of upper arms 5 and a pair of lower arms 6 connected therewith by means of a pair of screws 7. The opening between upper arms 5 and the lower arms 6 is adjusted by adjusting the degree of tightness of screws 7. A degree of tension between the femur 1 and tibia 2 is checked in the following manner. First, upper arms 5 and lower arms 6 are closed (in contact) and are inserted between femur 1 and tibia 2. Then the opening between arms 5 and the lower arms 6 is then expanded by rotating screws 7. During this operation, the surgeon finds a degree of proper tension of the ligaments with his perception or senses based on his experience as sensing a stress applied to his fingers during rotation of screws 7, thus setting a suitable spacing between the femur 1 and tibia 2. Thereafter, expander 4 is removed from the knee joint, a distance of the spacing between upper arms 5 and lower arms 6 is measured, and an artificial joint having a size corresponding to this distance is selected. Then the selected artificial joint is embedded between femur 1 and tibia 2.

Figure 1:
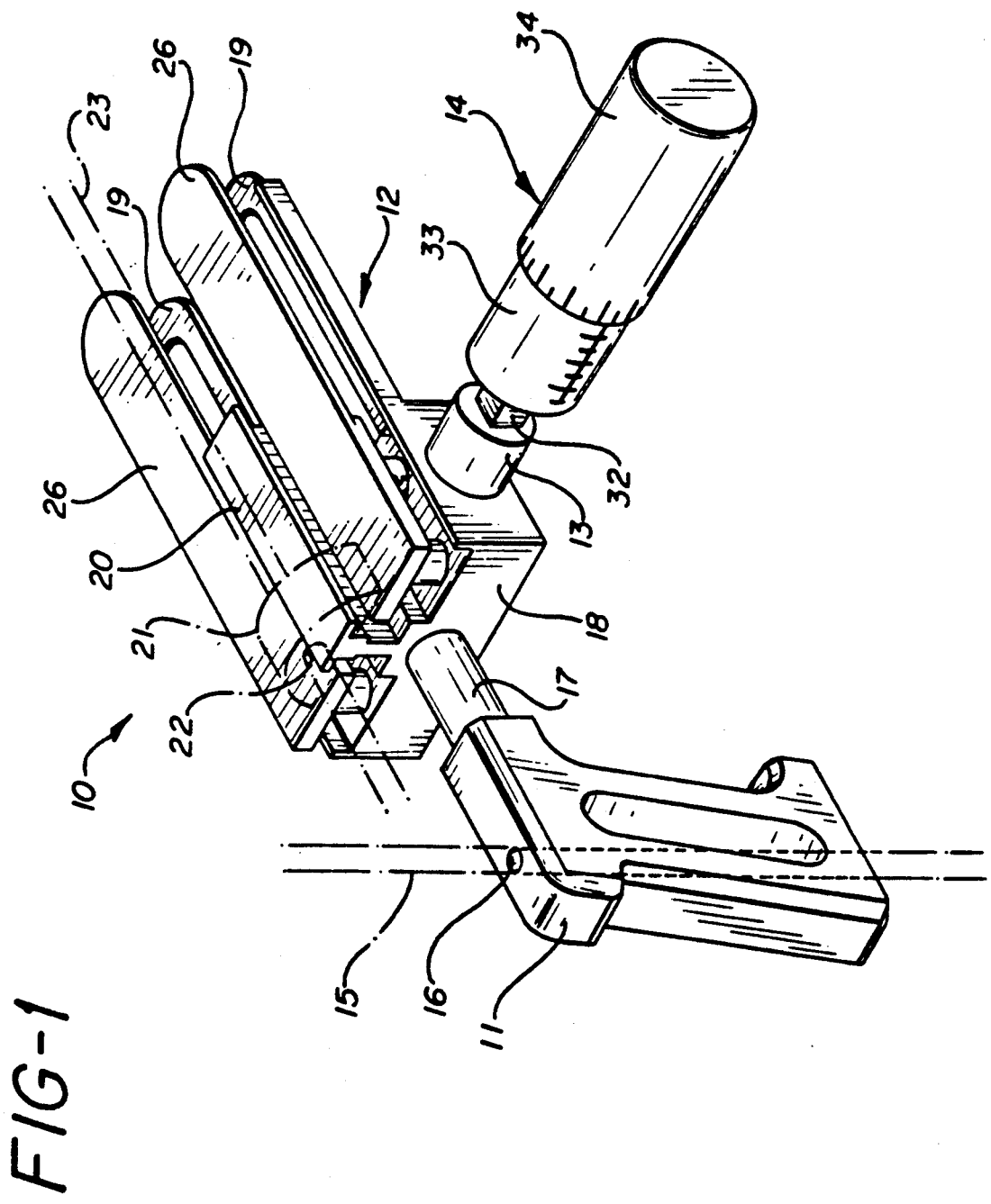
FIG. 1 is a schematic perspective view of the tension meter for orthopedic surgery according to a first preferred embodiment of the present invention.
Figure 2:
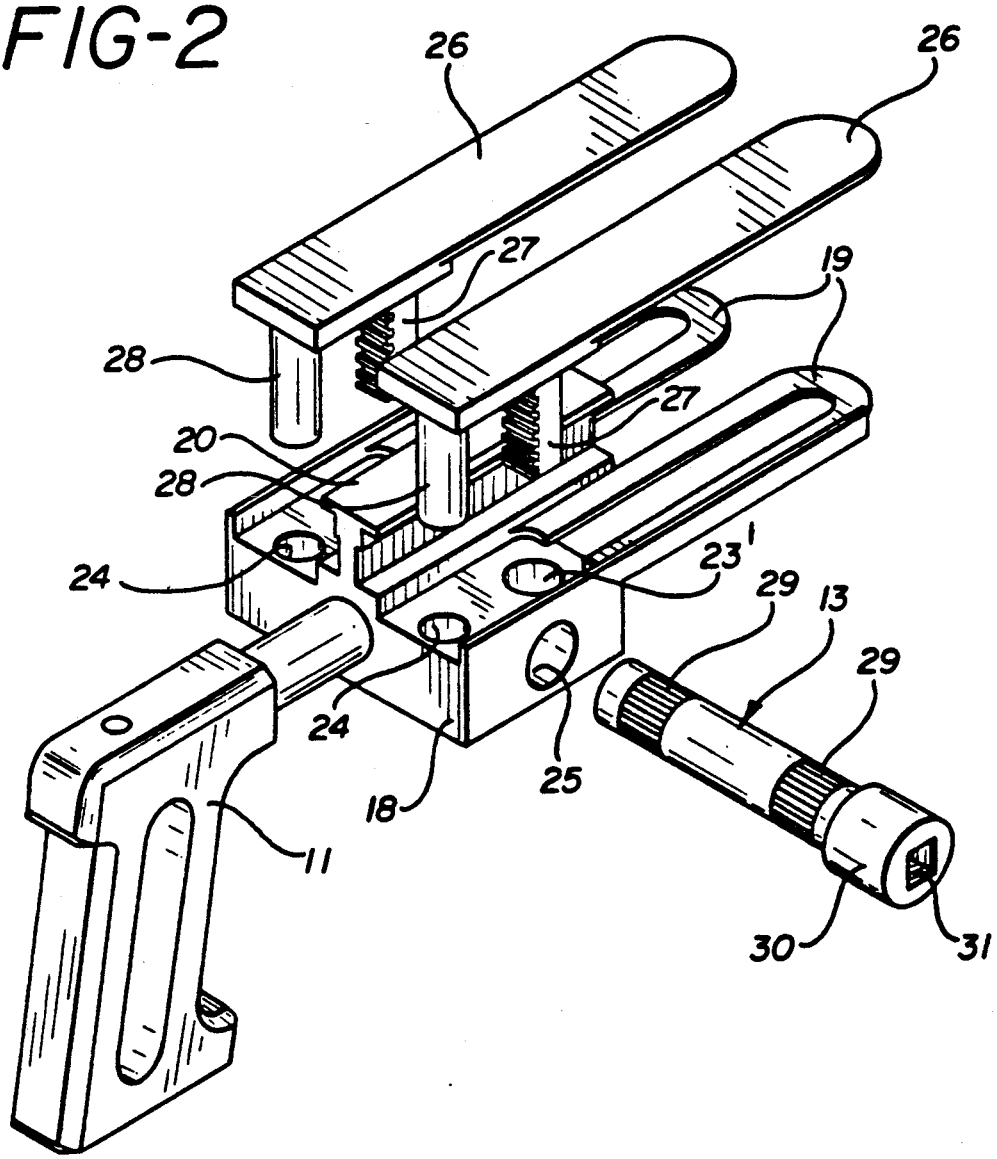
FIG. 2 is an exploded perspective view of the tension meter shown in FIG. 1.
Figure 3:
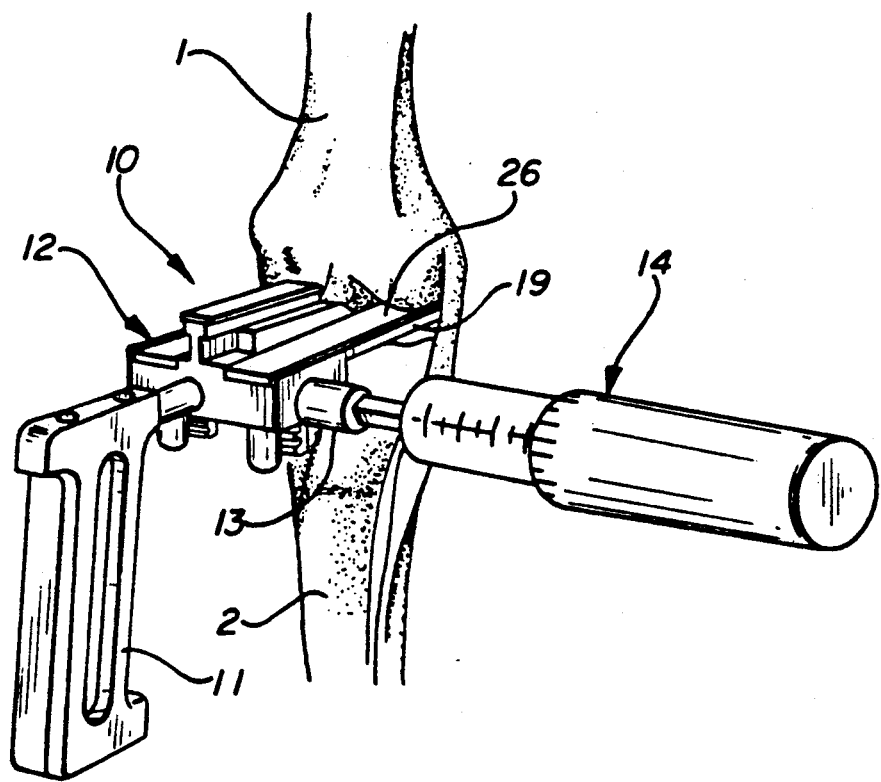
FIG. 3 is a perspective view showing the use of the tension meter shown in FIG. 1 for the substitution of an artificial joint for a knee joint.

Referring to FIGS. 1-3, reference numeral 10 generally designates a tension meter of the present invention for use in orthopedic surgery (which will be hereinafter be referred to as a tension meter). Tension meter 10 is primarily used to measure the degree of tension between a femur 1 and a tibia 2 before implanting an artificial knee joint. In the preferred embodiment, tension meter 10 is generally constructed of a grip portion 11, a tension meter body 12 mounted to the grip portion 11, and a torque setting device 14 rotatably connected through a torque shaft 13 to the tension meter body 12.

Grip portion 11 is formed like a pistol grip, and it is adapted to be gripped by a hand to thereby support tension meter 10 as a whole. Grip portion 11 is formed with a vertical through-hole 16 for inserting a vertical positioning rod 15 and supporting the same. Rod 15 is used for positioning tension meter 10 in such a manner that rod 15 is vertically erected through hole 16 of grip portion 11, and is then made parallel to tibia 2 to thereby make perpendicular to the tibia 2 a longitudinal direction of movable arms 26 and fixed arms 19 which will be hereinafter described. Tension meter body 12 is integrally connected through a connecting rod 17 to an upper front end of grip portion 11.

Tension meter body 12 is comprised of a rectangular parallelepiped block portion or body portion 18, a pair of fixed arms 19 extending frontwardly from the block portion 18, and a positioning portion 20 formed at a central portion of an upper surface of the block portion 18. The fixed arms 19 extend to the opposite side of the grip portion 11, and each of fixed arms 19 has an arcuate front end. Fixed arms 19 are adapted to be inserted between femur 1 and tibia 2 so as to be positioned on the tibia 2 side. Fixed arms 19 are arranged in suitably spaced relationship from each other so as to correspond to two ligaments connecting opposite side portions of femur 1 and tibia 2 with each other, so that when they are inserted between femur 1 and tibia 2, they are prevented from being deflected.

Positioning portion 20 projects from the upper surface of block portion 18 at the transversely central position thereof, and extends from grip portion 11 side to the fixed arms 19 side. A semi-cylindrical mounting member 21 is detachably mounted on a rear end portion of positioning portion 20. Mounting member 21 is formed at its central portion with a through-hole 22 extending in a longitudinal direction of positioning portion 20. A horizontal positioning rod 23 is adapted to be inserted through through-hole 22 of mounting member 21. Rod 23 functions similarly to rod 15. That is, rod 23 is used for positioning the tension meter 10 in such a manner that rod 23 is inserted through hole 22 of mounting member 21 so as to be made parallel to positioning portion 20, and tension meter 10 is adjusted in position so as to be made parallel to femur 1 under a normally bent condition of a knee, thereby making the longitudinal direction of fixed arms 19 parallel to femur 1.

Referring to FIG. 2, there is shown block portion 18 which is formed with a pair of vertical through-holes 23' on the right and left sides of positioning portion 20 and a pair of vertical through-holes 24 on the right and left sides of the positioning portion 20. That is, through-holes 23' formed on fixed arms 19 side are arranged in parallel to through-holes 24 formed on grip portion 11 side. As will be hereinafter described, through-holes 23' are formed to receive a pair of rack gears 27, and through-holes 24 are formed to receive a pair of supporting rods 28. Further, block portion 18 is formed on its one side surface with a horizontal hole 25 for receiving the torque shaft 13. Hole 25 is communicated with through-holes 23 in block portion or body portion 18, so that torque shaft 13 can mesh with rack gears 27 in block portion 18.

A pair of movable arms 26 are provided on the upper surface of block portion 18 so as to be movable away therefrom. Movable arms 26 are formed as substantially rectangular elongated plate-like members, and they are disposed just above fixed arms 19, respectively. Similarly to fixed arms 19, each of movable arms 26 has an arcuate front end. Each rack gear 27 and each supporting rod 28 project downwardly from a lower surface of each movable arm 26. Each rack gear 27 has a gear portion directed to grip portion 11 side, and is movably inserted into corresponding through-hole 23 of block portion 18. Each supporting rod 28 formed as a round rod is arranged on the rear side of each rack gear 27, and is movably inserted into corresponding through-hole 24 of the block portion 18.

Thus, both movable arms 26 are mounted on the upper surface of block portion 18 so as to be movable away therefrom by movably inserting rack gears 27 into through-holes 23' and movably inserting supporting rods 28 into the through-holes 24. An outer diameter of each supporting rod 28 is set to be slightly smaller than an inner diameter of each through-hole 24, so that when the movable arms are inclined by a load applied to the front ends of movable arms 26, movable arms 26 cannot be vertically moved.

Torque shaft 13 is rotatably inserted in hole 25 of block portion 18. Torque shaft 13 is comprised of a small-diameter round rod portion and a large-diameter portion 30 formed at a rear end of the small diameter portion. The small diameter portion of torque shaft 13 is formed with front and rear pinion portions 29 adapted to mesh with rack gears 27 of the movable arms 26 under the condition where torque shaft 13 is inserted in hole 25. Large diameter portion 30 of torque shaft 13 has an outer diameter larger than an inner diameter of hole 25. Accordingly, when torque shaft 13 is rotated in hole 25, movable arms 26 are vertically moved above block portion 18 by a pair of rack-and-pinion mechanisms formed by pinion portions 29 and rack gears 27.

Large diameter portion 30 of torque shaft 13 is formed at its rear end with a connecting hole 31 for connecting torque setting device 14 to torque shaft 13. The connecting hole 31 has a square opening for receiving a connecting shaft 32 having a square cross-section which will be hereinafter described.

As shown in FIG. 1, torque setting device 14 is detachably mounted to the torque shaft 13. Such torque setting devices are well known and may be purchased from Tohnichi Corp. in Japan as their RTD series torque setting devices. Torque setting device 14 is comprised of the rectangular prismatic connecting shaft 32 adapted to be fitted with the connecting hole 31 of the torque shaft 13, a columnar set load dial portion 33 incorporating a rear end portion of the connecting shaft 32, and a columnar adjusting portion 34 rotatably connected to set load dial portion 33. Further, torque setting device 14 includes a torque limiter mechanism constructed by a known technique. That is, the torque limiter mechanism functions to limit a torque to be transmitted to connecting shaft 32 to a value less than an adjusted biasing force of a spring incorporated in the torque setting device 14. More specifically, in torque setting device 14, a load is set by rotating adjusting portion 34 relative to the set load dial portion 33 prior to engagement of connecting rod 32 into connecting hole 31, and making a position of the front end surface of adjusting portion 34 accord with a desired dial of the set load dial portion 33. At this time, the biasing force of the spring incorporated in torque setting device 14 is adjusted to a value corresponding to the above set load by the rotation of adjusting portion 34 relative to the set load dial portion 33. Thereafter, the connecting rod 32 is brought into engagement with the connecting hole 31, and the adjusting portion 34 is further rotated to rotate torque shaft 13 through connecting rod 32. When a load applied to the connecting rod 32 becomes equal to the above set load during the rotation of torque shaft 13, the rotation of connecting shaft 32 by rotation of the adjusting portion 34 in a direction of application of the load is stopped to start idling of the adjusting portion 34.

With use of tension meter 10 as constructed above, an artificial joint is substituted for a knee joint in the following manner. First, prior to engagement of connecting rod 32 into connecting hole 31, adjusting portion 34 is rotated relative to the set load dial portion 33 to set a torque value corresponding to a degree of tension of the ligaments of a patient according to a strength of the ligaments on the basis of past data or the like. After setting the torque value, connecting rod 32 is inserted into the connecting hole 31 of torque shaft 13. At this time, movable arms 26 are maintained in contact with upper surface of block portion 18. That is, no gap is present between the movable arms 26 and the fixed arms 19. Further, rack gears 27 of movable arms 26 are meshed with pinion portions 29 of torque shaft 13.

Then, as shown in FIG. 3, the front end portions of fixed arms 19 and movable arms 26 are inserted between femur 1 and tibia 2 of the patient. Under this condition, adjusting portion 34 is rotated to rotate torque shaft 13 through connecting rod 32. As a result, movable arms 26 are lifted away from block portion 18 by rack-and-pinion mechanisms formed by pinion portions 29 and rack gears 27 by the rotation of torque shaft 13. That is, the opening between the movable arms 26 and the fixed arms 19 is increased to thereby expand the opening between the femur 1 and the tibia 2 and stretch the ligaments. On the other hand, a reaction force produced by the contraction force of the ligaments is applied to fixed arms 19 and movable arms 26. Then, this force is transmitted through rack gears 27 of movable arms 26, torque shaft 13 and the connecting shaft 32 to the torque limiter mechanism in torque setting device 14. When the force thus transmitted becomes equal to the set torque value of the torque limiter mechanism, adjusting portion 34 starts idling to thereby stop the lifting of movable arms 26. That is, relative displacement of movable arms 26 in relation to the fixed arms 19 is limited by the torque limiter mechanism.

After the opening between femur 1 and tibia 2 is expanded so as to obtain the preliminarily set load value (i.e., a value converted from a degree of tension of the ligaments or a value converted from a distance of the opening or gap between femur 1 and tibia 2; and which set value corresponds to the degree of tension or the distance), the surgeon checks whether or not a stretch condition of the ligaments is optimum by touching the ligaments with his/her fingers or swinging a leg portion below the joint in right, left, front and rear directions.

Until the optimum stretch condition of the ligaments is obtained, the above operation is repeated, that is the gap between femur 1 and tibia 2 is expanded so as to correspond to the preliminarily set load value by lifting the movable arms 26. When the optimum stretch condition is obtained, the spacing between movable arms 26 and fixed arms 19 at this time is measured. Then, an artificial joint having a size corresponding to this measured spacing is selected and then implanted.

Utilizing tension meter 10 as described above, the degree of tension of the ligaments can be adjusted to a value set by the torque limiter mechanism on the basis of past data or the like. Accordingly, unlike the prior art such that an artificial joint is selected merely by surgeon's senses, the present invention can make it possible to select an artificial joint quantitatively or more precisely. Furthermore, since the quantitative data is recorded, a highly reproducible surgical operation can be carried out based on accumulated data.

Figure 4:
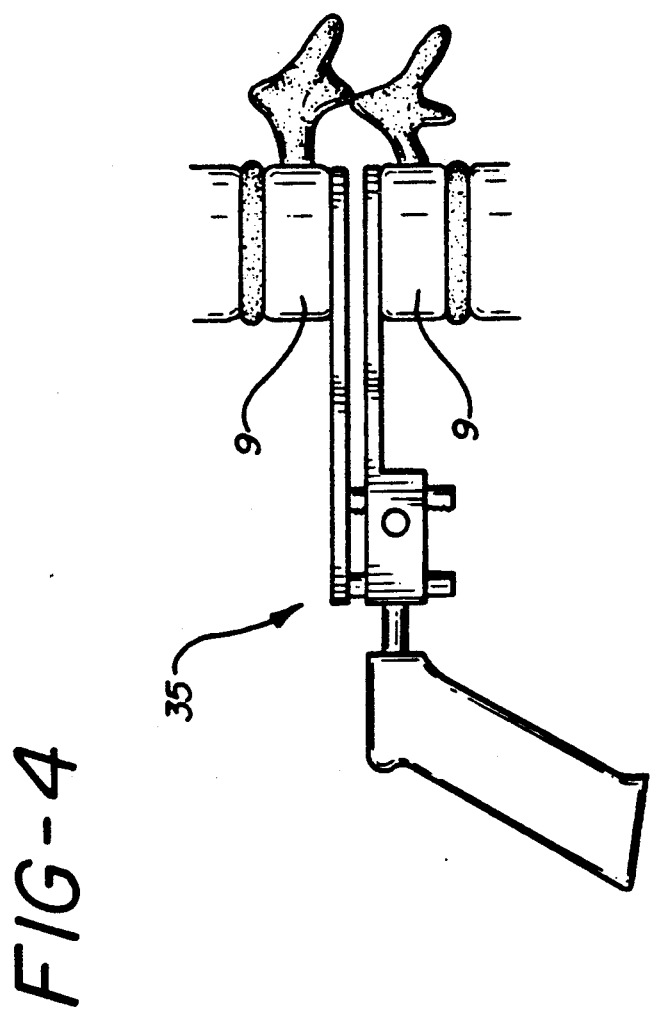
FIG. 4 is a side view showing the use of the tension meter according to the present invention for the implantation of an artificial bone for fixing a vertebral body.

FIG. 4 shows a second preferred embodiment of the present invention in which the tension meter for orthopedic surgery is used for implanting an artificial bone to fix a vertebral body. By using a tension meter 35 instead of the conventional spreader 8 shown in FIG. 8, an artificial bone can be implanted quantitatively or precisely without the reliance upon surgeon's senses, and a highly reproducible surgical operation can be carried out in the same manner as in the first preferred embodiment using the tension meter 10 shown in FIGS. 1-3. However, unlike tension meter 10 to be used for substitution of an artificial joint for a knee joint, tension meter 35 to be used for fixation of a vertebral body does not require a pair of movable arms and a pair of fixed arms, but only requires a single movable arm and a single fixed arm.

If a single movable arm and a single fixed arm are provided when replacing a knee joint, it is difficult to uniformly stretch the ligaments connecting the opposite side portions of the femur and the tibia upon insertion of the single movable arm and the single fixed arm into the opening between both the bones for expanding the gap. Therefore, it is preferable to provide a pair of movable arms and a pair of fixed arms when using the tension meter in replacing a knee joint with a prosthesis. However, when implanting an artificial bone between vertebral bodies 9, since many ligaments are present between vertebral bodies 9, a sufficient balance can be obtained upon expansion of a spacing between the vertebral bodies 9 by using a single movable arm and a single fixed arm.

Figure 8:
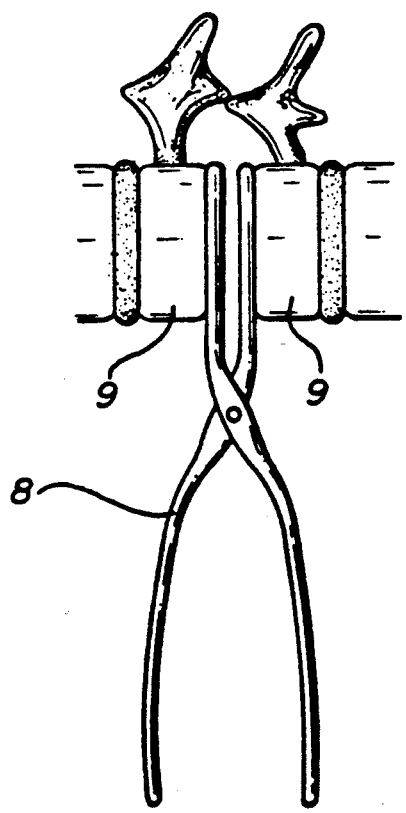
FIG. 8 is a side view explaining a further conventional method of the surgical operation in the case of implanting an artifical bone between vertebral bodies.

In the case of implanting an artificial bone for fixing a vertebral body, an intervertebral disk present at an implantation position is first cut away prior to implantation of the artificial bone. Then a front end portion of a spreader 8 (as shown in FIG. 8) is inserted between adjacent vertebral bodies 9, and the opening therebetween is spread by using the spreader 8. Then, the artificial bone is implanted into this opening. In this case, a degree of spreading of the opening between the vertebral bodies 9 relies on X-ray measurement carried out before the surgical operation or macroscopic measurement of a distance between the vertebral bodies 9 during the surgical operation.

Figure 5:
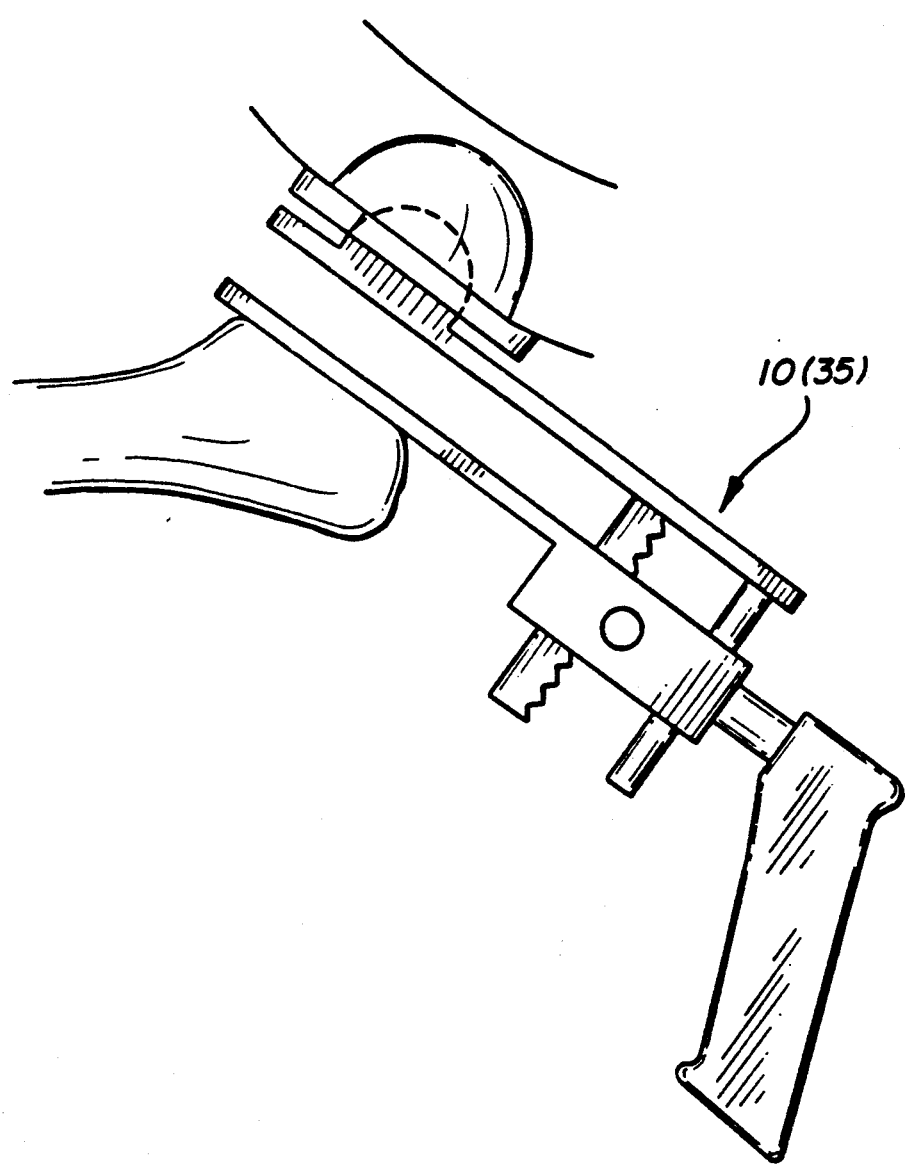
FIG. 5 is a side view showing the use of the tension meter according to the present invention for the substitution of an artificial joint for a hip joint.

Although the tension meter for orthopedic surgery in the above preferred embodiments is applied to the substitution of an artificial joint for a knee joint and the implantation of an artificial bone for fixing a vertebral body, the present invention may be applied to the substitution of an artificial joint for a hip joint, for example, as shown in FIG. 5.

As described above, according to the tension meter for orthopedic surgery of the present invention, a degree of tension of a ligament can be preliminarily set by the torque limiter mechanism on the basis of past data or the like. Accordingly, the space between bones can be expanded properly and quantitatively by the fixed arm and the movable arm without the reliance upon surgeon's senses as in the prior art. As a result, an artificial joint or an artificial bone can be precisely selected. Furthermore, since quantitative data is left, a surgical operation with high reproducibility can be carried out owing to accumulation of the data, thereby expediting the surgical operation and increasing the reliability of the surgical operation While several examples of the present invention have been described, it is obvious that many changes and modifications may be made thereunto, without departing from the spirit and scope of the invention.

We claim:

1. A tension meter for orthopedic surgery for expanding openings between bones and measuring a degree of tension between said bones before implanting a prosthetic device bone between the bones, the tension meter comprising:

a grip portion, a tension meter body mounted to said grip portion, a torque shaft operatively coupled to said body, said torque shaft having gear teeth formed therein, and a torque setting device rotatably connected through said torque shaft to said tension meter body, said torque setting device including means for measuring torque and limiting the torque to a predetermined value;

said tension meter body comprising a body portion, a fixed arm extending from one end of said body portion and a movable arm mounted on an upper surface of said body portion so as to be movable away therefrom, said movable arm being located above said fixed arm in opposed relationship thereto, said movable arm being provided with a gear portion for meshing with the gear teeth on said torque shaft; said torque setting device including a means on said torque shaft for limiting torque by limiting relative displacement of said movable arm away from said fixed arm and therefore the force applied to the bone between said fixed arm and said movable arm is limited by said predetermined torque value.

2. The tension meter as set forth in claim 1 wherein said gear portion on said movable arm is in the form of a rack and said gear teeth on said torque shaft are in the form of a pinion.

3. The tension meter as set forth in claim 1 wherein, a second removable arm is mounted on said upper surface of said body portion.

4. The tension meter as set forth in claim 1 wherein said torque setting device includes means for measuring and displaying the torque generated by the force applied between said fixed arm and said movable arm.

5. A tensioning device for setting the tension of ligaments extending between two bones during orthopedic surgery comprising:

a body portion having a first arm extending therefrom for engaging the first of the bones and a second arm for engaging the second of the bones moveable with respect to said first arm and extending generally parallel thereto, said second arm having a drive portion extending through said body, said drive portion having gear teeth formed thereon;

a torque shaft extending through said body, said torque shaft having gear teeth formed thereon in meshing engagement with said gear teeth on said drive portion; and means for pre-setting the tension of the ligaments including means mounted on said torque shaft for pre-setting the torque generated thereon, said means for pre-setting further including a means for limiting the movement of said first and second arms away from one another against the tension in the ligaments to a predetermined distance.

6. The tension meter as set forth in claim 5 wherein said drive portion on said movable arm is in the form of a rack and said gear teeth on said torque shaft are in the form of a pinion.

7. The tension meter as set forth in claim 5 wherein said second arm comprises a pair of arms mounted on said body portion.

8. The tension meter as set forth in claim 5 wherein said torque setting device includes means for measuring and displaying the torque generated by the force applied between said fixed arm and said movable arm.

* * * * *